US006468562B2

(12) United States Patent
Moilanen et al.

(10) Patent No.: US 6,468,562 B2
(45) Date of Patent: *Oct. 22, 2002

(54) BETAINE PRODUCT, METHOD FOR ITS MANUFACTURE, AND ITS USE

(75) Inventors: Raija Moilanen, Piispanristi; Helena Hallanoro, Naanatali, both of (FI)

(73) Assignee: Cultor Corporation, Helsinki (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,617

(22) PCT Filed: May 28, 1998

(86) PCT No.: PCT/FI98/00449

§ 371 (c)(1),
(2), (4) Date: Jan. 27, 2000

(87) PCT Pub. No.: WO98/53907

PCT Pub. Date: Dec. 3, 1998

(65) Prior Publication Data

US 2002/0048605 A1 Apr. 25, 2002

(30) Foreign Application Priority Data

May 28, 1997 (FI) .................................................. 97 2264

(51) Int. Cl.[7] .................................................. A61K 9/16
(52) U.S. Cl. ........................ 424/490; 424/630; 427/212; 427/334; 514/772
(58) Field of Search ................................. 424/490, 630; 427/212, 334; 514/772

(56) References Cited

U.S. PATENT DOCUMENTS

| 3,580,519 | A | * | 5/1971 | Klein et al. ................... 241/22 |
| 3,708,574 | A | * | 1/1973 | Corker ......................... 424/44 |
| 5,062,994 | A | | 11/1991 | Imperatori ................... 252/545 |
| 5,695,784 | A | * | 12/1997 | Pollinger et al. ........... 424/495 |

FOREIGN PATENT DOCUMENTS

| EP | 0 781 554 A1 | 7/1997 |
| FR | 2151076 A | 4/1973 |
| FR | 2518426 A1 | 6/1983 |
| WO | 8102429 A1 | 9/1981 |
| WO | 9535022 A1 | 12/1995 |

OTHER PUBLICATIONS

WPI/Derwent's abstract, No. 75–43835W, week 7526, Abstract of SU, 438407 (As Kirg Org Chem), Jan. 28, 1975, abstract.
WPI/Derwent's abstract, No. 78–83702A, week 7825, Abstract of SU, 586889 (As Kirg Org Chem), Jan. 6, 1978, abstract.
WPI/Derwent's abstract, No. 78–26128A, week 7814, Abstract of JP, 53018725 (Kyowa Fermentation KK), Feb. 21, 1978, abstract.
Derwent Abstract SU–1745252, Jul. 7, 1992.

* cited by examiner

Primary Examiner—Thurman K. Page
Assistant Examiner—Lakshmi Channavajjala
(74) Attorney, Agent, or Firm—Nixon & Vanderhye P.C.

(57) ABSTRACT

Solid betaine products having good treatment, fluidity and moisture resistance properties are prepared by arranging a hydrophobic, moisture-proof layer of a fluidity-improving anti-agglomeration agent on the surfaces of glycine betaine anhydride or monohydrate crystals or particles. Animal feeds containing these betaine products are described.

20 Claims, No Drawings

BETAINE PRODUCT, METHOD FOR ITS MANUFACTURE, AND ITS USE

FIELD OF THE INVENTION

The invention relates to a solid betaine product having good treatment properties. The invention also relates to a method for the manufacture of the betaine product, and its use, as well as an animal feed containing said betaine product and other feed components.

BACKGROUND OF THE INVENTION

Betaines are fully N-methylated amino acids. Betaines are natural products that have an important function in both plant and animal metabolism. One of the most common betaines is a glycine derivative in which three methyl groups are bonded to the nitrogen atom of the glycine molecule. This betaine compound is usually called betaine, glycine-betaine or trimethylglycine, and it has the following structural formula:

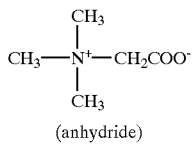

(anhydride)

Other betaines include, for example, alaninebetaine and proline-betaine, which has been reported, among other things, to prevent osteomalacia in chickens. A detailed description of betaines is given by R. G. Wyn Jones and R. Storey in *The Physiology and Drought Resistance in Plants*, ed. L. G. Paleg and D. Aspinall, Academic Press, Sydney, Australia, 1981.

Betaine thus has a bipolar structure and it contains several chemically reactive methyl groups, which it can donate in enzyme-catalysed reactions. Most organisms are able to synthesize small quantities of betaine e.g. for the methyl function, but they are not able to react to stress by substantially increasing the production and storage of betaine.

Betaine is a highly hygroscopic substance, and therefore its treatment and use as such or as part of an end product causes problems in humid conditions, since it turns viscous, lumpy and poorly flowable. In order to treat and use betaine without problems, it is necessary to protect it against humidity. Hydrophilic fluidity improvers/anti-agglomeration agents (which absorb free water) have been used previously. However, hydrophilic substances of his kind are not able to protect betaine in humid conditions, even though they improve the fluidity of betaine in good, dry conditions.

Betaine is used, among other things, as a feed additive and as a crop improver of plants under stress conditions, as well as in cosmetic, pharmaceutical and food industries.

Betaine can be obtained, for example, from sugar beet by chromaographic methods. Betaine is commercially available e.g. under the registered trademark BETAFIN®, Cultor Oy, Finnsugar Bioproducts. BETAFIN® is solid betaine (betaineanhydride or betainemonohydrate) produced by Finnsugar Bioproducts.

EP 0 573 876 discloses a method for the manufacture of a product containing cholinechloride by mixing cholinechloride solution in fine drops with a pulverized, hydrophobic substance, and by drying the mixture with a fluidized bed drier. Silica made hydrophobic by silanization or a metallic salt of a fatty acid can be used as the hydrophobic substance.

BRIEF DESCRIPTION OF THE INVENTION

Now it has been found that by means of hydrophobic substances a moisture-proof layer can be arranged on the surface of betaine particles. Hence fluidity and anti-agglomeration of a betaine product, its use as such or as a part of the end-product, can substantially be improved also in humid conditions. Hydrophobic substance is preferably added to a betaine product by utilizing an efficient blender.

DETAILED DESCRIPTION OF THE INVENTION

The invention relates to a solid betaine product which contains a fluidity improver and/or anti-agglomeration agent. In accordance with the invention, a hydrophobic, moisture-proof layer is arranged on the surface of particles.

The solid betaine product refers to a crystalline or ground product. The particle size of the crystalline product is 0.05 to 2.0 mm, preferably on the average about 0.3 to 0.6 mm. Preferably, the crystalline product does not contain practically any dustlike substance, i.e. particles with the diameter of less than about 0.01 mm. The particle size of the ground product is 1 to 100 μm.

The hydrophobic layer on the surface of the particles may consist of a metallic salt of a fatty acid, such as calcium or magnesium stearate, or hydrophobic silica. Additionally, a substance which enhances said hydrophobic substance to adhere to or spread onto the surface of betaine particles may be present on the surface of the crystals.

Suitable substances that enhance the adhesion or spreading of the hydrophobic substance comprise fats, oils, fat-like substances, such as lecithins and waxes, and water-insoluble substances, such as cellulose derivatives and silicone derivatives.

In accordance with the invention, a new betaine product can be produced, for example, by mixing the blend of betaine and a hydrophobic, moisture-proof substance.

In the method of the invention, various mixers can be used. When only powdery hydrophobic substance is used, suitable mixers comprise various batch mixers or continuous mixers, such as drum mixers or helical/screw mixers. Mixing time depends on the power of the mixer, and also on the batch size. The object is that the hydrophobic substance mixes as evenly as possible with the betaine. In the ideal case, the powder forms a monomolecular layer on the surface of the product. Preferably, the smallest betaine crystals are screened out before a treatment with the hydrophobic substance.

When a binding agent is added to the powdery hydrophobic substance, spray granulators or fluidized bed drying/coating devices can be used in the method of the invention, in addition to various batch mixers and continuous mixers.

Various grinders, such as an air jet grinder or a turbo mill or some other mill useful for grinding sugar crystals, can be used in the method of the invention. The betaine is thus ground with the powdery hydrophobic substance, and the obtained powdery product flows freely and it will not agglomerate.

In accordance with one preferred method of the invention, melted, hot (e.g. about 40° C. higher than the melting point) fat is first sprayed onto the surface of the betaine crystals. It is preferable to use a hydrogenated fat with a high melting point, whereby a product is obtained, which retains good fluidity (does not become viscous) even at tropical temperatures. Other fats/oils can also be used (depending on the use of the product). When using oils that are fluid at room temperature, no heating is needed. When using fats with a high melting point, it is preferable to preheat the betaine crystals close to the melting point of the fat. This facilitates the forming of a layer as even as possible. Thereafter the surface of the warm crystal coated with fat is 'powdered' with a hydrophobic substance. Managing the processing conditions is critical (temperatures) in order that even and comprehensive protection is achieved, and the product does not stick to the walls of the equipment or elsewhere, and the product remains single, flowable crystals (no agglomeration).

Instead of spraying the fat, another technique may also be used, in which the betaine particles and the solid fat flakes, et cetera, are first mixed together. Thereafter, the blend is heated to exceed the melting point of the fat while it is continuously being mixed.

The fat treatment may be carried out by using a mixer with the possibility of adding liquid (spray nozzle systems) or a spray granulator or devices of the type of fluidized bed drier/coater.

Useful hydrophobic substances include, for example, the following:

Metallic salts of long-chain fatty acids:
Stearates:
metallic salts of stearic acid in powder form,
(melting point in excess of 150° C.)
e.g. Ca-stearate, Ceasit Leviss, manufactured by Bärlocher, Germany
Ca-stearate CPR-2, manufactured by Akcros Chemicals V.O.F., Holland
Silica-based hydrophobic substances:
e.g. Sipernat D17, manufactured by Degussa Ltd., Germany
Aerosil R972, manufactured by Degussa Ltd., Germany
(and other hydrophobic Sipernat and Aerosil products)
Cellulose derivatives:
e.g. Ethocel, manufactured by Dow USA (in powder form)

Useful substances that enhance the adhesion or spreading of the hydrophobic substance include, for example, the following:

Fats:
Revel S (acetylized monoglyceride, hydrogenated soy oil); melting point 63° C.; manufactured by Loders Croklaan, Holland
Revel C; melting point 58° C.,
Revel F; melting point 46° C.,
Revel AC; melting point 37° C.,
Dynasan P 60; manufactured by Huls AG, Germany
Oils:
Fish oils
Lecithins:
e.g. lecithins of Metarin product line; manufactured by Lucas Mayer, Germany
Silicone derivatives (spraying in solution):
e.g. Pharsil MK silicone emulsion; manufactured by: Wacker Chemie GmbH, Germany
Cellulose derivatives (spraying in solution):
e.g. Ethocel; manufactured by Dow USA

EXAMPLE 1

Betaine anhydride (Nutristim, manufactured by Cultor Oy; quantity 50 kg, granule size 0.27 to 1.0 mm) was introduced into a drum mixer (Forberg F-60, manufactured by Fa. Halvor Forberg A/S, Norway) and 3 kg calcium stearate (Ceasit Leviss, manufactured by Barlocher, Germany, particle size 99% <71 μm) was added thereto. Mixing was carried out at room temperature for about three minutes. The obtained product had good fluidity, and it remained fluid for at least three hours at a temperature of 30° C., the relative air humidity being 95%.

EXAMPLE 2

Into a continuous screw mixer (length of the mixing worm 4 m, diameter 400 mm, two mixing points in the screw, manufactured by Siirtoruuvi Oy, Finland) were fed betaine anhydride (Nutristim, manufactured by Cultor Oy; granule size 0.27 to 1.0 mm) 5,000 kg/hour and 6% calcium stearate (Ceasite Leviss, manufactured by Barlocher, Germany; particle size 99% <71 μm) through an additive dispenser (Accurate, manufactured by Accurate Dry Material Feeders inc., USA). Mixing was carried out continuously in the mixing helix/screw. Temperature was 20° C. and duration of mixing in the mixing helix was two minutes. The obtained product had good fluidity and it remained fluid at least for three hours at a temperature of 30° C., the relative air humidity being 95%.

EXAMPLE 3

Betaineanhydride (Nutristim, manufactured by Cultor Oy; quantity 47.5 kg, granule size 0.27 to 1.0 mm) was introduced into a drum mixer (Forberg F-60, manufactured by Fa. Halvor Forberg A/S, Norway) and preheated to 55° C. Thereafter 2.5 kg hot (100° C.) fat (Revel-S, manufactured by Loders Croklaan, Holland) was added by spraying (nozzle size 4004, pressure 3 bar) and simultaneously mixing (for 1.3 minutes). Finally, 1 kg calcium stearate (Ceasit Leviss, manufactured by Bärlocher, Germany; particle size 99% <71 μm) was added, and the blend was cooled to 30° C. and mixed for 3.7 minutes. The obtained product's solubility in water was poor and fluidity was good: it remained fluid at least for three hours at a temperature of 30° C., the relative air humidity being 95%.

EXAMPLE 4

The test was conducted in the same way as in Example 1, but instead of calcium stearate, hydrophobic silica (Sipernat D 17, manufactured by Degussa, Germany; average granule size 10 μm) was used. The obtained product was very fluid, and it remained fluid at least for three hours at a temperature of 30° C., the relative air humidity being 95%.

EXAMPLE 5

The test was conducted in the same way as in Example 3, but instead of calcium stearate, hydrophobic silica (Sipernat D 17, manufactured by Degussa, Germany; average granule size 10 μm). The obtained product's solubility in water was poor and fluidity was good: it remained fluid at least for three hours at a temperature of 30° C., the relative air humidity being 95%.

EXAMPLE 6

Betainemonohydrate (technical quality, manufactured by Cultor Oy; quantity 47.5 kg, granule size 0.25 to 1.25 mm) was introduced into a drum mixer (Forberg F-60, manufactured by Fa. Halvor Forberg A/S, Norway) and preheated to 55° C. Thereafter, 1.5 kg hot (100° C.) fat (Revel-S, manufactured by Loders Croklaan, Holland) was added by spraying (nozzle size 4004, pressure 3 bar) and simultaneously mixing (for 1.3 minutes). Finally, 1.5 kg calcium stearate (Ceasit Leviss, manufactured by Barlocher, Germany; particle size 99% <71 μm) was added, and the blend was cooled to 30° C. and mixed for 3.7 minutes. The obtained product's solubility in water was poor and fluidity was good.

EXAMPLE 7

The test was conducted in the same way as in Example 6, but instead of calcium stearate, hydrophobic silica (Sipernat D 17, manufactured by Degussa, Germany; average particle size 10 μm) was used. The obtained product had good fluidity and it remained fluid at least for three hours at a temperature of 30° C., the relative air humidity being 95%.

EXAMPLE 8

Betaineanhydride (Betafin BP, manufactured by Cultor Oy; particle size 0.05 to 1.0 mm) was fed into a continuous air jet grinder (Pulva FP Micronization, manufactured by Oy Finnpulva Ab); simultaneously, hydrophobic silica (Aerosil R 972, manufactured by Degussa; average particle size 16 nm) was also fed into the grinder. The total quantity of betaineanhydride was 400 kg and that of silica 4 kg (1%). The average grinding fineness of the obtained product was less than 20 μm, the product was very fluid and it did not agglomerate.

What is claimed is:

1. A solid betaine product which contains a hydrophobic fluidity improver and/or an anti-agglomeration agent, arranged as a hydrophobic, moisture-proof layer on the surfaces of glycine betaine anhydride or monohydrate crystals or particles thereof wherein the layer consists of a metallic salt of a fatty acid.

2. The product of claim 1 wherein the layer consists of calcium stearate or magnesium stearate.

3. A solid betaine product which contains a hydrophobic fluidity improver and/or an anti-agglomeration agent, arranged as a hydrophobic, moisture-proof layer on the surfaces of glycine betaine anhydride or monohydrate crystals or particles thereof wherein the layer consists of hydrophobic silica.

4. A solid betaine product which contains glycine betaine anhydride or monohydrate crystals or particles,
   a hydrophobic fluidity improver and/or an anti-agglomeration agent, arranged as a hydrophobic, moisture-proof layer on the surfaces of glycine betaine anhydride or monohydrate crystals or particles wherein the layer consists of a metallic salt of a fatty acid, and also
   a substance which enhances the hydrophobic substance to adhere or to spread is additionally arranged on the surface of the crystals or particles.

5. The product of claim 4 wherein the layer consists of calcium stearate or magnesium stearate.

6. A solid betaine product which contains glycine betaine anhydride or monohydrate crystals or particles,
   a hydrophobic fluidity improver and/or an anti-agglomeration agent, arranged as a hydrophobic, moisture-proof layer on the surfaces of glycine betaine anhydride or monohydrate crystals or particles wherein the layer consists of hydrophobic silica, and also
   a substance which enhances the hydrophobic substance to adhere or to spread is additionally arranged on the surface of the crystals or particles.

7. The product of claim 4 or 6 wherein the substance which enhances adherence or spread is selected from the group consisting of a fat, oil, lecithin, wax, a water-insoluble cellulose derivative and a water-insoluble silicon derivative.

8. A process of preparing a solid betaine product which contains a metallic salt of a fatty acid as a hydrophobic fluidity improver and/or an anti-agglomeration agent, arranged as a hydrophobic, moisture-proof layer on the surfaces of glycine betaine anhydride or monohydrate crystals or particles, said process comprising mixing together the glycine betaine anhydride or monohydrate crystals or particles with the hydrophobic agent.

9. The process of claim 8 wherein the hydrophobic agent is calcium stearate or magnesium stearate.

10. A process of preparing a solid betaine product which contains hydrophobic silica as a hydrophobic fluidity improver and/or an anti-agglomeration agent, arranged as a hydrophobic, moisture-proof layer on the surfaces of glycine betaine anhydride or monohydrate crystals or particles, said process comprising mixing together the glycine betaine anhydride or monohydrate crystals or particles with the hydrophobic agent.

11. The process of claim 8 wherein the crystals or particles are mixed with hydrophobic silica.

12. The process of claim 8 or 10 wherein the particles or crystals are ground with the hydrophobic agent.

13. The process of claim 8 or 10 wherein prior to mixing the hydrophobic agent with glycine betaine an oil or melted fat is first arranged on the surface of the crystals or particles and thereafter the hydrophobic agent is arranged on the surface of the crystals or particles.

14. The process of claim 13 wherein the melted fat is a hydrogenated fat with a melting point 40° C. or higher and the crystals or particles are preheated prior to mixing to about the melting point of the fat.

15. The process of claim 8 or 10 wherein prior to mixing the crystals or particles with the hydrophobic agent the crystals or particles are blended with a solid fat, the hydrophobic agent is added and thereafter the blend is heated to melt the fat melting while the blend is continuously mixed.

16. An animal feed composition comprising the product of claim 1 or 3.

17. A fertilizer composition comprising the product of claim 1 or 3.

18. A cosmetic skin care product or toiletry composition comprising the product of claim 1 or 3.

19. A pharmaceutical composition comprising the product of claim 1 or 3.

20. A food product composition comprising the product of claim 1 or 3.

* * * * *

UNITED STATES PATENT AND TRADEMARK OFFICE
CERTIFICATE OF CORRECTION

PATENT NO. : 6,468,562 B2  
DATED : October 22, 2002  
INVENTOR(S) : Moilanen et al.

Page 1 of 1

It is certified that error appears in the above-identified patent and that said Letters Patent is hereby corrected as shown below:

<u>Title page,</u>
Item [73], delete, "[73] Assignee: Cultor Corporation
                                    Helsinki Finland"
and insert -- [73] Assignee: Finnfeeds Finland Oy
                                    Espoo, Finland --

Signed and Sealed this

Twenty-fifth Day of November, 2003

JAMES E. ROGAN
*Director of the United States Patent and Trademark Office*